US011419979B2

(12) United States Patent
Schaffer et al.

(10) Patent No.: US 11,419,979 B2
(45) Date of Patent: Aug. 23, 2022

(54) VARIABLE FLUID FLOW RATE CONTROL DEVICE

(71) Applicant: Avent, Inc., Alpharetta, GA (US)

(72) Inventors: Andrew Schaffer, Costa Mesa, CA (US); Mark D. Mendillo, Mission Viejo, CA (US)

(73) Assignee: Avent, Inc., Alpharetta, GA (US)

( * ) Notice: Subject to any disclaimer, the term of this patent is extended or adjusted under 35 U.S.C. 154(b) by 143 days.

(21) Appl. No.: 15/754,079

(22) PCT Filed: Aug. 27, 2015

(86) PCT No.: PCT/US2015/047143
§ 371 (c)(1),
(2) Date: Feb. 21, 2018

(87) PCT Pub. No.: WO2017/030594
PCT Pub. Date: Feb. 23, 2017

(65) Prior Publication Data
US 2018/0280614 A1    Oct. 4, 2018

(51) Int. Cl.
*A61M 5/168* (2006.01)
*A61M 5/14* (2006.01)
(Continued)

(52) U.S. Cl.
CPC ........ *A61M 5/16813* (2013.01); *A61M 5/141* (2013.01); *A61M 5/142* (2013.01);
(Continued)

(58) Field of Classification Search
CPC .......... A61M 5/16813; A61M 5/16881; A61M 5/16877; A61M 2205/3331; A61M 39/22;
(Continued)

(56) References Cited
U.S. PATENT DOCUMENTS 2,239,842 A * 4/1941 Evans ................ F16K 37/0016
116/277
3,434,694 A * 3/1969 Skinner .................... F16K 1/04
251/215
(Continued)

FOREIGN PATENT DOCUMENTS

JP        2010057860 A    3/2010
WO    WO 2004/026373 A1    4/2004
(Continued)

OTHER PUBLICATIONS

International Search Report and Written Opinion for PCT/US2015/047143, dated Mar. 8, 2016, 17 pages.
Co-Pending U.S. Appl. No. 15/754,095, filed Feb. 21, 2018.

*Primary Examiner* — Tiffany Legette
*Assistant Examiner* — Antarius S Daniel
(74) *Attorney, Agent, or Firm* — Meunier Carlin & Curfman LLC

(57) ABSTRACT

A flow selector having features for controlling the flow rate of a fluid over a continuous range of flow rates is provided. In particular, a flow selector including a flow rate selection mechanism is provided, where the flow rate selection mechanism provides more precise control of the fluid flow rate. A flow selector comprising a needle valve for controlling the flow rate of a fluid over a continuous range of flow rates also is provided.

23 Claims, 7 Drawing Sheets

(51) Int. Cl.
  *A61M 5/142* (2006.01)
  *A61M 5/148* (2006.01)
  *A61M 5/165* (2006.01)

(52) U.S. Cl.
  CPC ........ *A61M 5/148* (2013.01); *A61M 5/16881* (2013.01); *A61M 5/165* (2013.01); *A61M 2205/0216* (2013.01); *A61M 2205/3334* (2013.01); *A61M 2205/583* (2013.01)

(58) Field of Classification Search
  CPC ..... A61M 2039/226; A61M 2205/3334; F16K 37/0016
  See application file for complete search history.

(56) References Cited

U.S. PATENT DOCUMENTS

| | | | |
|---|---|---|---|
| 3,443,789 A * | 5/1969 | Bucklin | F16K 1/02 251/214 |
| 4,269,387 A | 5/1981 | Reynolds et al. | |
| 4,300,552 A * | 11/1981 | Cannon | A61M 5/16813 137/513.5 |
| 4,332,369 A * | 6/1982 | Gordon | A61M 5/16877 251/114 |
| 4,425,113 A * | 1/1984 | Bilstad | A61M 39/28 251/9 |
| 4,431,009 A * | 2/1984 | Marino, Jr. | A61B 5/0215 600/486 |
| 4,471,942 A * | 9/1984 | Kocanowski | A61M 5/16877 251/115 |
| 4,589,872 A | 5/1986 | Bellin et al. | |
| 4,834,108 A * | 5/1989 | Vaillancourt | A61B 5/0215 600/486 |
| 5,080,652 A | 1/1992 | Sancoff et al. | |
| 5,105,983 A | 4/1992 | Sancoff et al. | |
| 5,254,481 A | 10/1993 | Nishida | |
| 5,318,515 A | 6/1994 | Wilk | |
| 6,350,253 B1 | 2/2002 | Deniega et al. | |
| 6,589,205 B1 | 7/2003 | Meadows | |
| 6,936,035 B2 | 8/2005 | Rake et al. | |
| 7,455,072 B2 | 11/2008 | Mabry et al. | |
| 8,308,688 B2 | 11/2012 | Valle et al. | |
| 8,968,242 B2 | 3/2015 | Tefera et al. | |
| 2003/0040722 A1 | 2/2003 | Massengale et al. | |
| 2013/0306172 A1* | 11/2013 | Volovec | F16K 1/12 137/556 |
| 2014/0243759 A1* | 8/2014 | Yoon | A61M 5/16881 604/250 |
| 2014/0323987 A1 | 10/2014 | Nelson et al. | |

FOREIGN PATENT DOCUMENTS

| | | |
|---|---|---|
| WO | WO 2005/028358 A2 | 3/2005 |
| WO | WO 2012/160495 A2 | 11/2012 |

\* cited by examiner

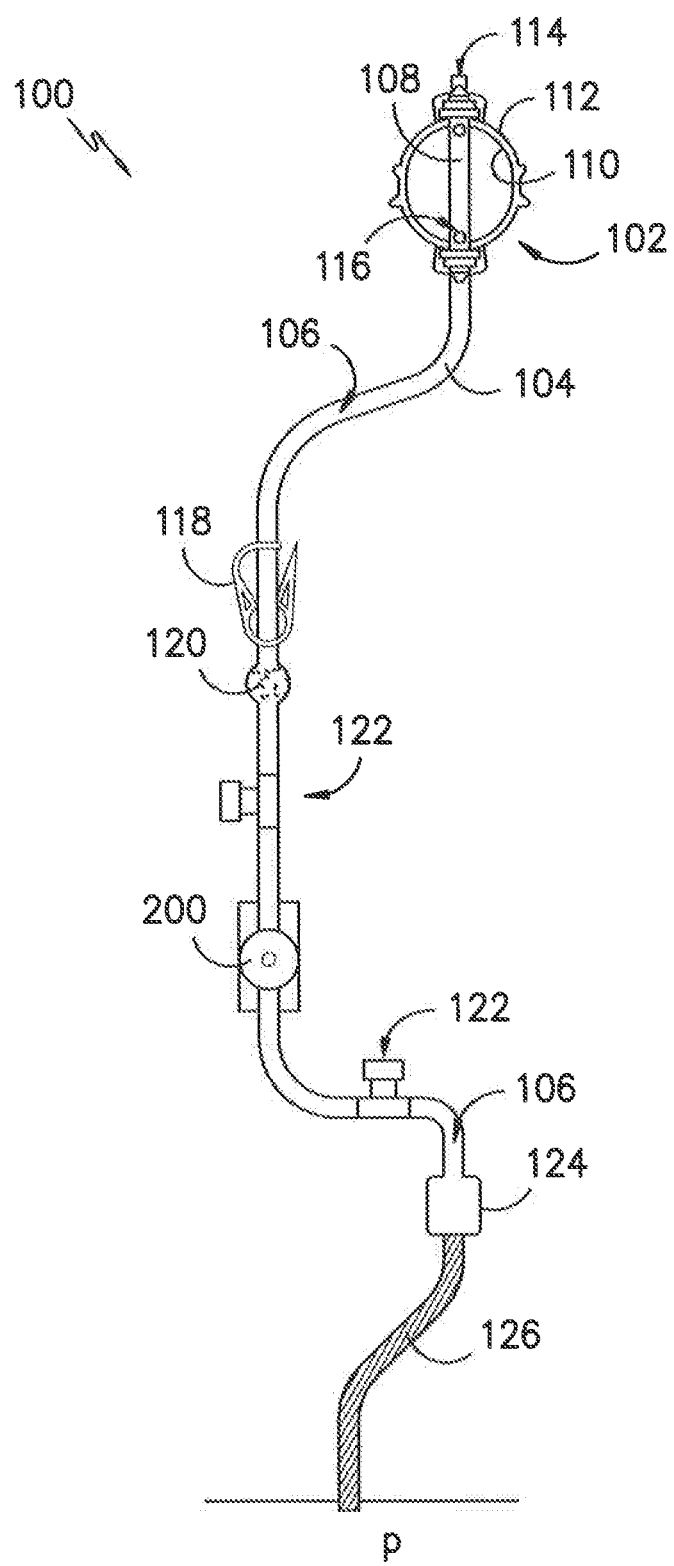
FIG. -1-

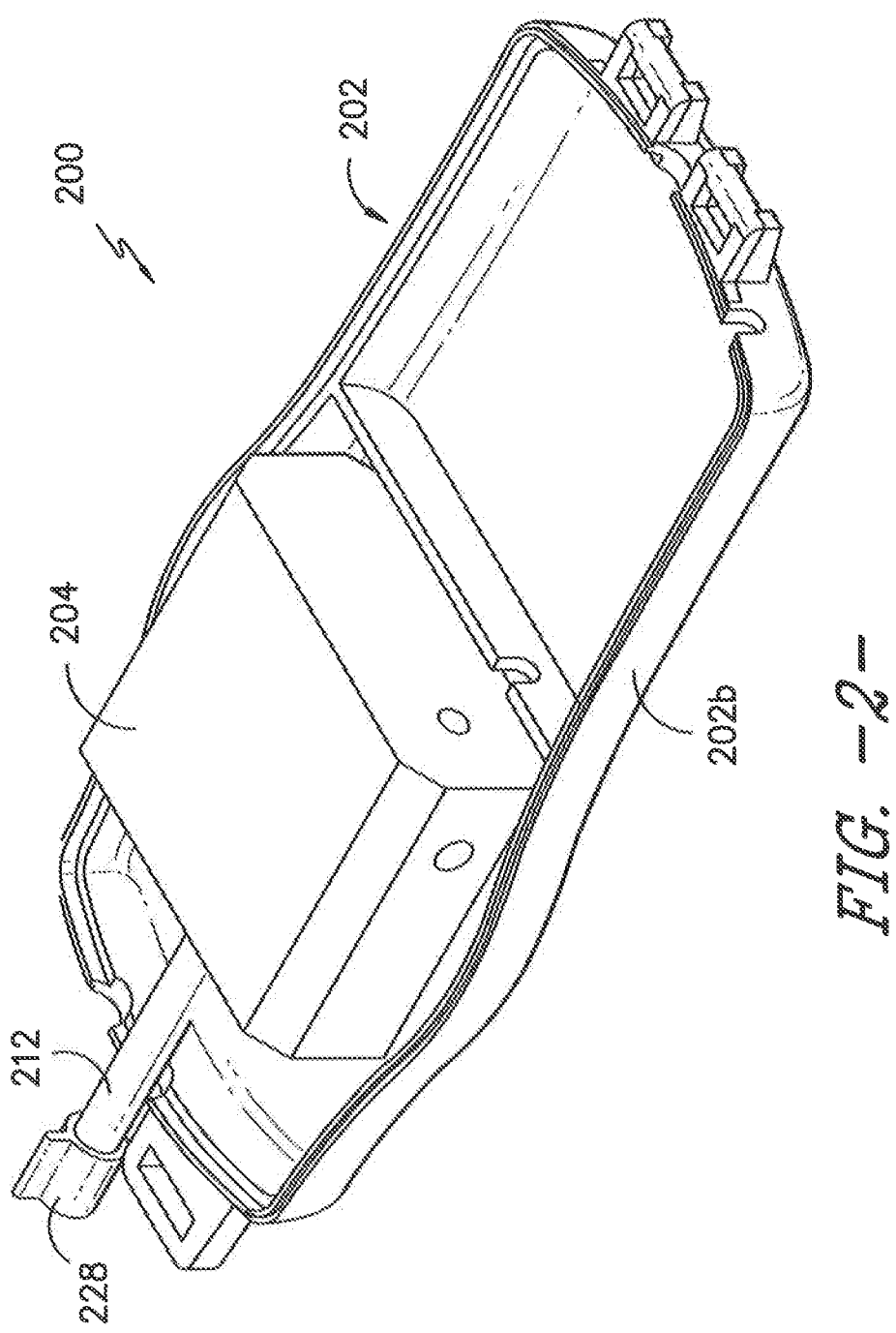

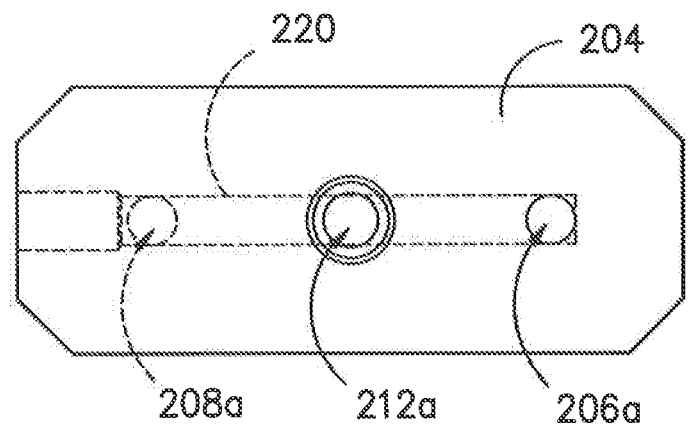
FIG. -3-
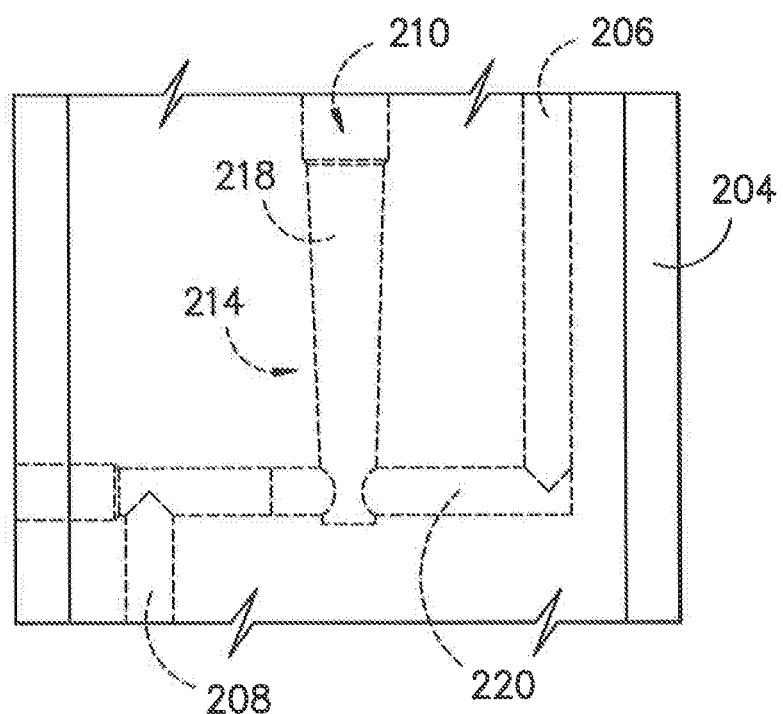
FIG. -4-

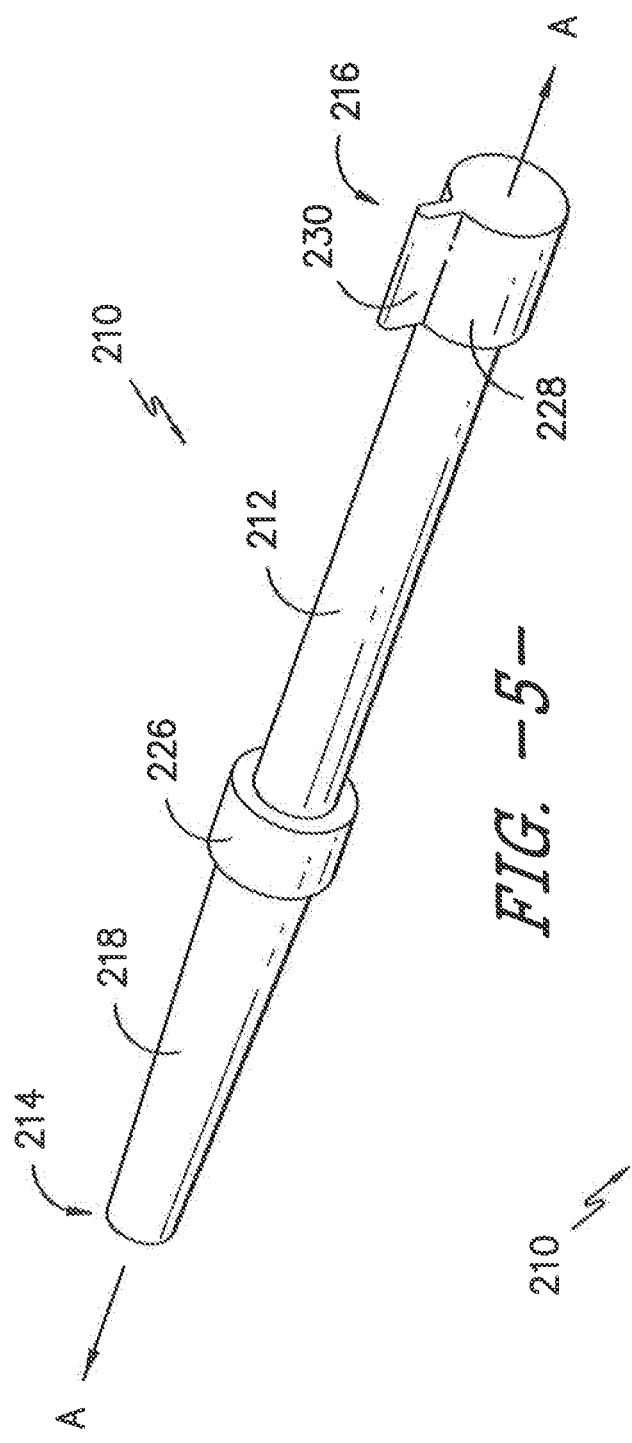
FIG. -5-
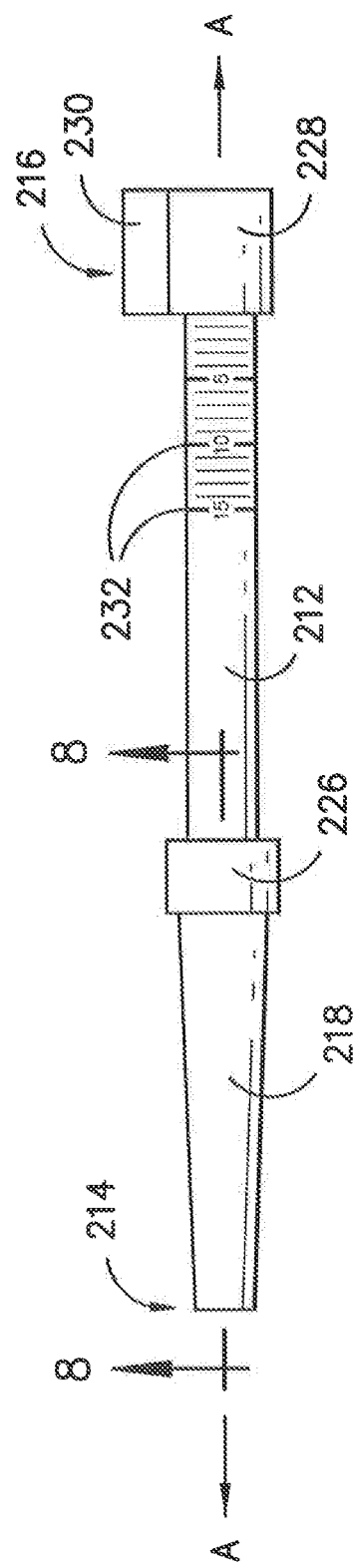
FIG. -6-

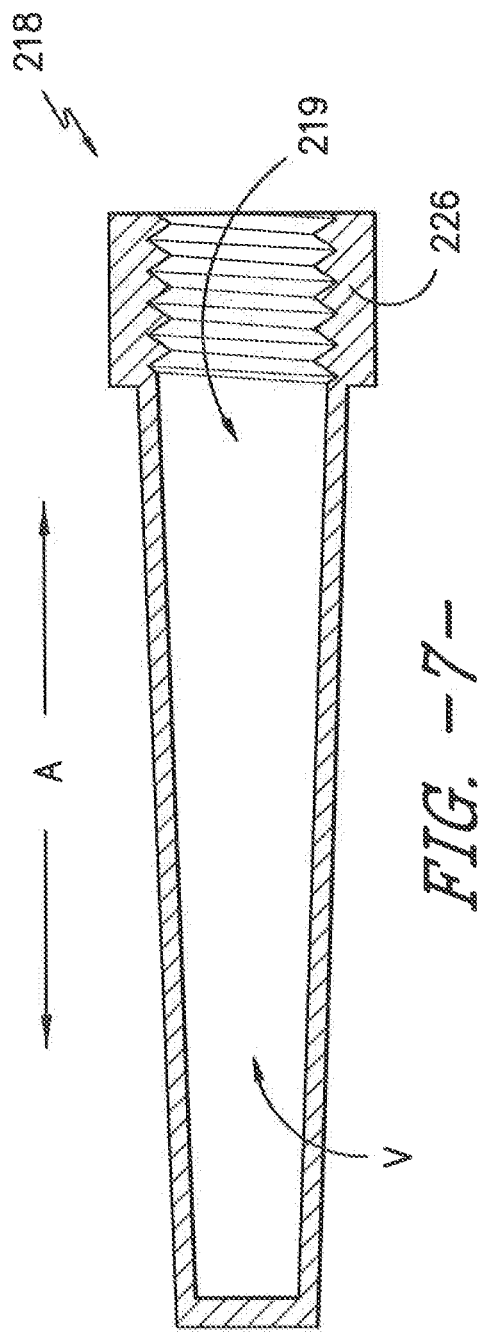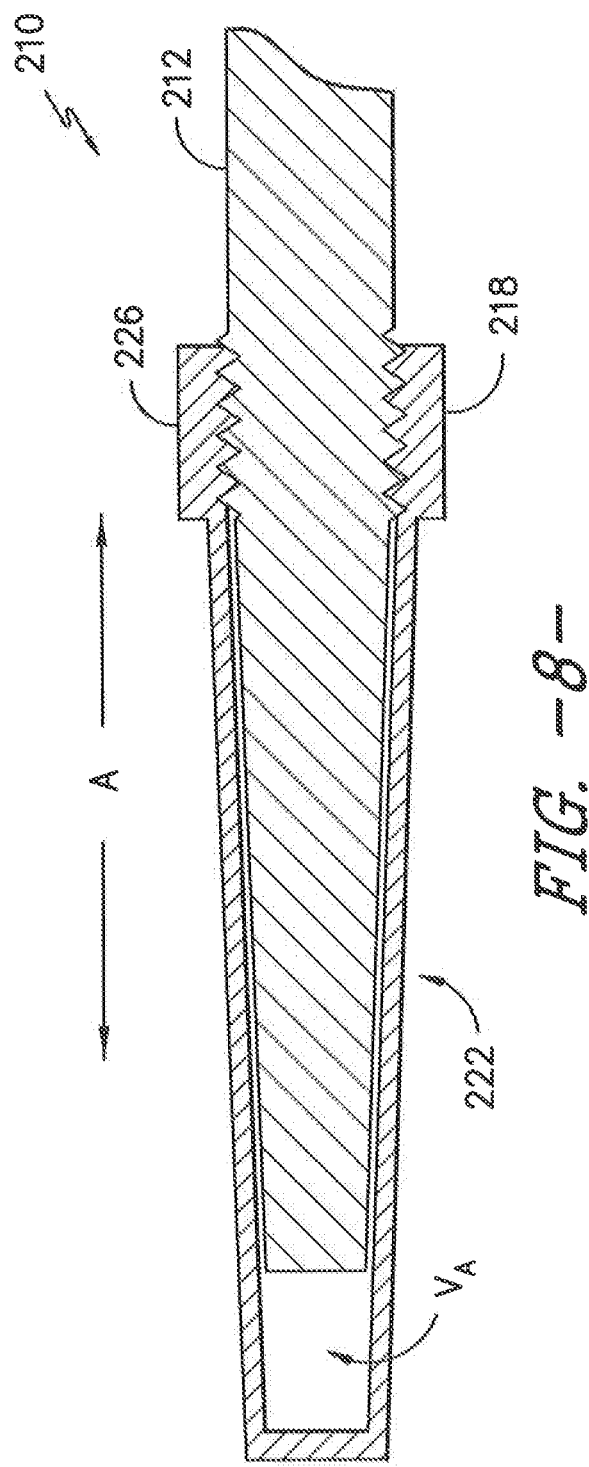

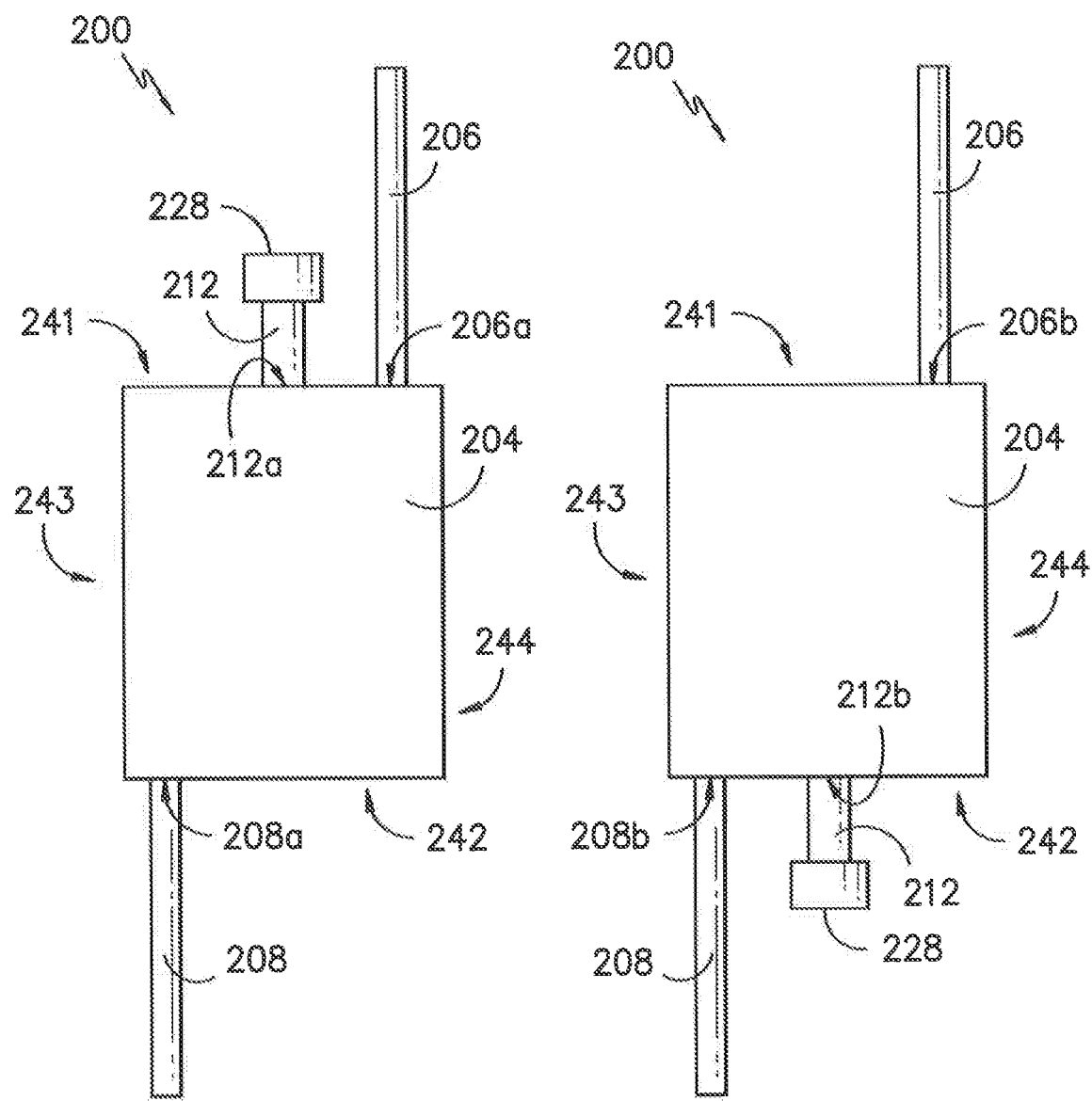
FIG. -9-  FIG. -10-

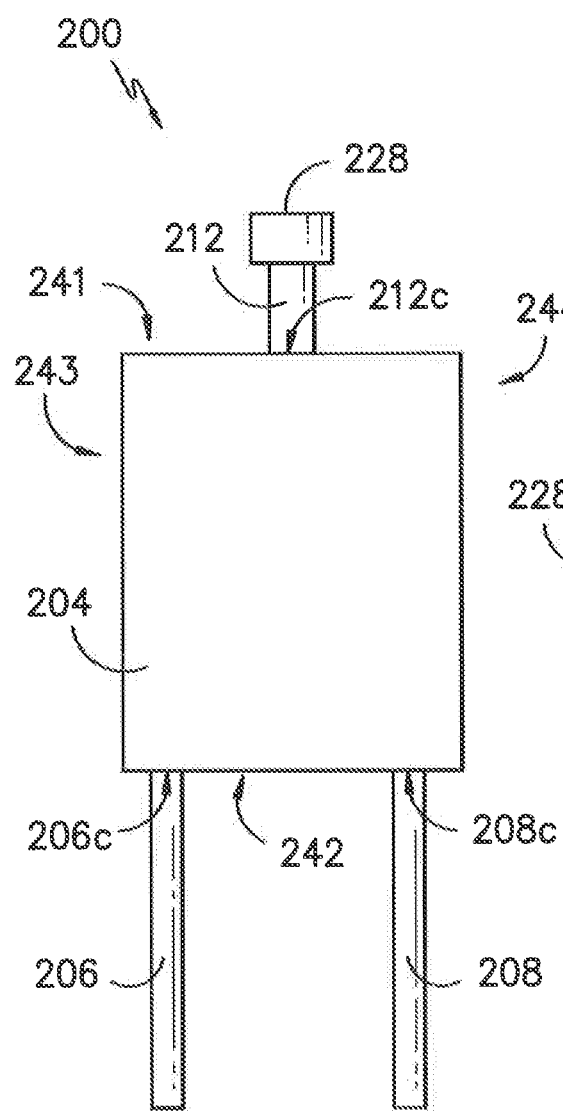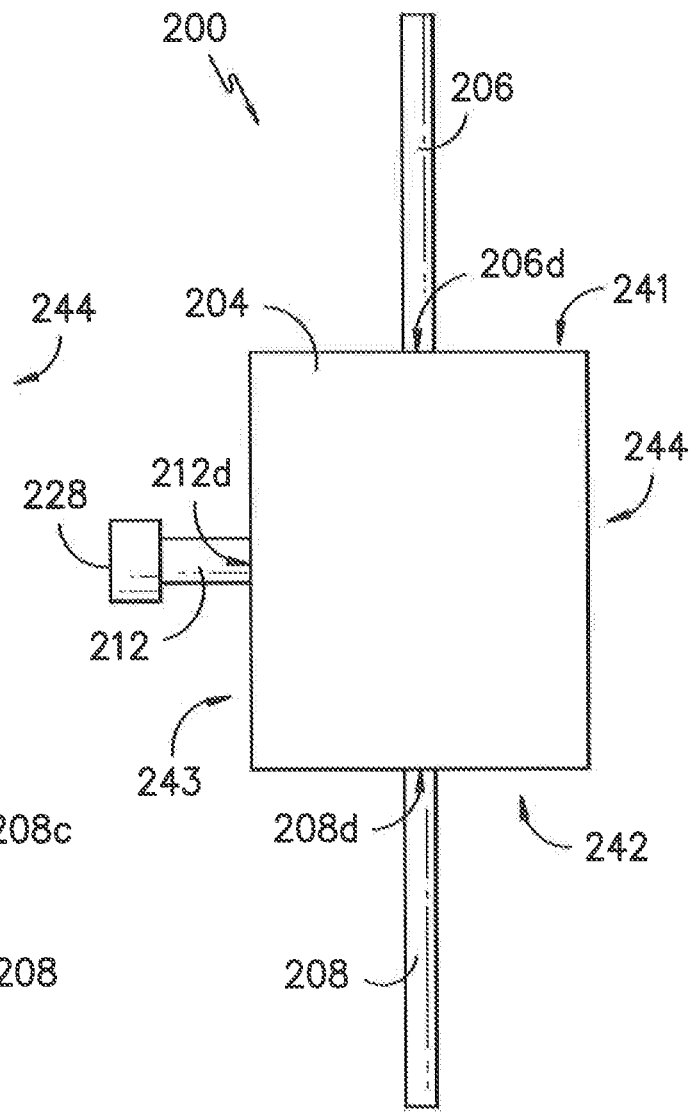
FIG. -11-  FIG. -12-

VARIABLE FLUID FLOW RATE CONTROL DEVICE

CROSS-REFERENCE TO RELATED APPLICATIONS

This application is a national phase of and claims priority to PCT/US2015/047143, filed Aug. 27, 2015, the contents of which are incorporated herein by reference thereto.

FIELD OF THE INVENTION

The present invention relates to fluid dispensing systems and devices for regulating the flow of fluids. More particularly, the present invention relates to a flow rate control device and, most specifically, to a catheter-based system for infusing a liquid into the body of a patient at a precisely controllable flow rate.

BACKGROUND

In the medical field, therapeutic or medicinal liquids are often administered to a patient by an infusion system. There are various types of infusion systems for delivering liquids to a catheter or needle. For example, in one system the liquid is typically contained in a reservoir (a bag or a bottle) suspended above the patient and is delivered through a tube, by the force of gravity. Alternatively, the liquid may be delivered from a reservoir by an infusion pump.

It is sometimes necessary to control the flow rate at which the liquid is delivered to the patient, particularly when the liquid is to be administered continuously over an extended period of time. The flow rate may be varied depending on, for example, the specific medical treatment, type of medicinal or therapeutic agent, or the specific needs of a particular patient. Indeed, a specific patient's need or demand for a particular drug or other agent may vary over time. Moreover, often the rates of flow are relatively low, in the range of from about 0.5 to about 14 cubic centimeters of fluid per hour, and are at relatively low pressures, e.g., less than about 4 pounds per square inch (28 kilopascals).

A variety of devices and techniques have been devised to control the flow rate at which liquid is delivered. An exemplary device is described in U.S. Pat. No. 5,318,515 for an "Intravenous Flow Regulator Device and Associated Method," issued to Wilk on Jul. 7, 1994. That device has a freely accessible slider member for selecting a desired flow rate from a range of discrete flow rates. Another device is described in U.S. Pat. No. 7,455,072 for a "Device for Selectively Regulating the Flow Rate of a Fluid" to Mabry et al., issued on Nov. 25, 2004. That device has a flow rate selection mechanism that is rotatable between positions corresponding to discrete flow rates; the discrete flow rates are achieved using flow control tubes of equal cross-sectional area and different lengths. Such a device may require using the Poiseuille equation to determine the length of tubing of a given diameter required to induce a predetermined flow rate. It can be labor intensive to determine the correct length of tube to match a pump pressure output, which may vary from lot to lot of pumps. Therefore, it may be desirable to diminish the manufacturing complexity of such devices to reduce manufacturing time and expense.

In addition to reducing manufacturing complexity, more precise control of the flow rate may be desirable. For example, it may be desirable or useful to adjust the flow rate over a continuous range of flow rates rather than over a range of defined incremental or discrete flow rates. Thus, there has been a need for a device that allows the selection of any flow rate over the entire range of available flow rates while maintaining reliability of the device, particularly for devices utilizing relatively low flow rates. There has been a further need for a device in which the selected flow rate is clearly indicated to a user of the device, such as the patient and/or the caregiver. Additionally, such a device should be easy and inexpensive to manufacture so that it may be economically made as a disposable item, while providing a high degree of reliability in use.

SUMMARY

The present invention provides a flow selector having features for selectively controlling the flow rate of a fluid over a continuous range of flow rates. In particular, a flow selector including a flow rate selection mechanism is provided, where the flow rate selection mechanism provides more precise control of the fluid flow rate. The present invention also provides a flow selector comprising a needle valve for selectively controlling the flow rate of a fluid over a continuous range of flow rates. Additional aspects and advantages of the invention will be set forth in part in the following description, may be apparent from the description, or may be learned through practice of the invention.

In a first exemplary embodiment, a flow selector for selectively controlling a flow rate of a fluid is provided. The flow selector includes an inlet tube; an outlet tube; and a flow rate selection mechanism. The flow rate selection mechanism has a shaft having a distal end and a proximal end, and a seat that receives the distal end of the shaft. The flow rate selection mechanism is positioned between the inlet tube and the outlet tube to permit an ingress of fluid from the inlet tube and an egress of fluid to the outlet tube. The flow selector further includes an enclosure for holding the inlet tube, the outlet tube, and the flow rate selection mechanism in position relative to each other. The enclosure has an inlet opening for receiving the inlet tube, an outlet opening for receiving the outlet tube, and a shaft opening for receiving the shaft of the flow rate selection mechanism.

In a second exemplary embodiment, a flow selector for selectively controlling a flow rate of a fluid is provided. The flow selector includes an inlet tube; an outlet tube; and a needle valve. The needle valve includes a shaft having a distal end and a proximal end, and a seat that receives the distal end of the shaft. The distal end of the shaft is tapered in shape and the seat has a recess with a shape complementary to the shape of the distal end of the shaft. The flow selector also includes an enclosure for holding the inlet tube, the outlet tube, and the needle valve in position relative to each other. The enclosure has an inlet opening for receiving the inlet tube, an outlet opening for receiving the outlet tube, and a shaft opening for receiving the shaft of the needle valve. The distal end of the needle valve is positioned between the inlet tube and the outlet tube within the enclosure to permit an ingress of fluid from the inlet tube and an egress of fluid to the outlet tube.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a schematic view of a device for dispensing fluid to a patient according to an exemplary embodiment of the present subject matter.

FIG. 2 provides a perspective view of a flow selector having a housing and an enclosure according to an exemplary embodiment of the present subject matter.

FIG. 3 provides an end view of the enclosure of FIG. 1 according to an exemplary embodiment of the present subject matter.

FIG. 4 provides a partial top view of the enclosure of FIG. 1 according to an exemplary embodiment of the present subject matter.

FIG. 5 provides a perspective view of a flow rate selection mechanism for a flow selector according to an exemplary embodiment of the present subject matter.

FIG. 6 provides a side view of the flow rate selection mechanism of FIG. 5 according to an exemplary embodiment of the present subject matter.

FIG. 7 provides a cross-section view of a seat of a flow rate selection mechanism according to an exemplary embodiment of the present subject matter.

FIG. 8 provides a cross-section view of a flow rate selection mechanism according to an exemplary embodiment of the present subject matter.

FIG. 9 provides a schematic view of a flow selector according to an exemplary embodiment of the present subject matter.

FIG. 10 provides a schematic view of a flow selector according to another exemplary embodiment of the present subject matter.

FIG. 11 provides a schematic view of a flow selector according to another exemplary embodiment of the present subject matter.

FIG. 12 provides a schematic view of a flow selector according to another exemplary embodiment of the present subject matter.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Referring to FIG. 1, the present subject matter encompasses a device 100 for dispensing fluid to a patient P and controlling the flow rate of the fluid through the device. Dispensing device 100 includes a reservoir 102 that serves as a pressurized fluid source or pump that holds medicinal fluid, such as local anesthetics (referred to hereinafter as a "pump") and that is configured to provide a source of fluid under pressure. Pump 102 forces the medicinal fluid through a conduit 104. Conduit 104 forms a continuous flow path 106 for delivery into a wound site nerve bundle or the blood stream of patient P.

In some configurations, dispensing device 100 may provide for bolus delivery. In such embodiment, conduit 104 splits into continuous or primary flow path 106 and into a controlled bolus flow path (not illustrated) for delivery into a wound site nerve bundle or the blood stream of patient P. Other aspects of the bolus delivery system are described more fully herein.

Pump 102 preferably accommodates about from 100 to 500 ml of fluid under a pressure of approximately 10 to 15 psi. Pump 102 has an inner core 108 surrounded by an elastomeric chamber 110 within a housing 112. Inner core 108 preferably has an inlet port 114 to fill the pump and an outlet port 116 in fluid communication with the conduit or tubing 104. Elastomeric chamber 110 is preferably constructed from a resilient material that may comprise a variety of elastomeric compositions, well known in the art, including vulcanized synthetic polyisoprenes, natural latex, natural rubber, synthetic rubber or silicone rubber. Exemplary pumps are described in U.S. Pat. No. 5,254,481, which is hereby incorporated by reference. A variety of other conventional pumps may be used, so long as they can impart the desired pressure on the fluid. For example, the pumps described in U.S. Pat. Nos. 5,080,652 and 5,105,983, which are hereby incorporated by reference may also be used, as well as other suitable electronic or mechanical pumps offered by other manufacturers as will be understood by those of skill in the art.

Fluid is held under pressure within elastomeric chamber 110 and flows from elastomeric chamber 110 through outlet port 116 into conduit 104 at a controlled and predictable rate. Alternatively, conduit 104 may be sized to serve as a flow restrictor.

An optional clamp 118 is positioned in the flow path 106 downstream from conduit 104. Clamp 118 can compress the flow path 106 such that fluid flow from pump 102 is occluded. Such occlusion is advantageous for the transportation and preparation of fluid delivery or dispensing device 100 as described herein. An exemplary clamp 118 also is described in U.S. Pat. No. 6,350,253, which is hereby incorporated by reference. However, a variety of other conventional clamps known in the industry may be used to occlude the flow of fluid from pump 102 through the flow path 106 such as, e.g., compression clamps, C clamps, roller clamps, and the like.

An optional filter 120 downstream of clamp 118 separates the fluid from contaminates and other undesired particles that may be found within the fluid. Filter 120 also preferably eliminates air from the fluid path 106. One such filter 120 is described in U.S. Pat. No. 6,350,253, which is hereby incorporated by reference. Other suitable filters recognized in the industry may be used to capture undesired particles and/or remove air from the system.

In some embodiments, device 100 for dispensing fluid to patient P utilizes at least one flow detector assembly 122 including a flow detector to indicate a flow condition. Desirably, one flow detector assembly 122 is located above or upstream of a flow selector 200 and one flow detector assembly 122 is located below or downstream of flow selector 200, as illustrated in FIG. 1. The particular arrangement of clamp 118, filter 120, and flow selector 200 herein described is merely exemplary. Clamp 118 and filter 120, if present, may be arranged with respect to flow selector 200 and the other components of dispensing device 100 in any order as will be easily understood by those skilled in the art.

Flow detector 122 provides a signal when the flow condition of the fluid in continuous flow path 106 has changed from a predetermined flow condition. Generally speaking, the flow rate in continuous flow path 106 can be associated with a fluid flow state such as, for example, a continuous and steady flow rate. For example, flow detector 122 may be configured to provide a signal that the flow rate of the fluid in continuous flow path 106 is less than the predetermined flow rate, within a range of predetermined flow rates, or greater than a predetermined flow rate.

As further illustrated in FIG. 1, conduit 104 may include an outlet or connection 124. Outlet 124 connects continuous flow path 106 to a catheter 126. Catheter 126 delivers the fluid into a wound site nerve bundle or the blood stream of patient P.

As previously stated, some embodiments of device 100 may incorporate a bolus delivery system. In an exemplary embodiment, the bolus delivery system accumulates a large quantity of fluid from the bolus flow path leading from reservoir 102 and holds the fluid under pressure until the bolus dose is triggered by a patient operable actuator for release into patient P. Such a large volume bolus delivery system is configured to receive fluid, elastically expand to pressurize fluid, store the pressurized fluid, and dispense the pressurized fluid, while avoiding bolus refill during bolus delivery or after bolus delivery but before it is enabled to elastically expand in a subsequent delivery cycle. The actuator is configured such that it does not require effort to force the fluid out of the bolus reservoir and such that when actuated by the patient, fluid is permitted to flow out of the bolus reservoir to the patient without further action by the patient. The large volume bolus delivery system is desirably a PCA device as described at, for example, U.S. Pat. No. 6,936,035 for "Patient Controlled Drug Administration Device" issued Aug. 30, 2005 to Rake et al. and U.S. Pat. No. 8,308,688 for "Large-Volume Bolus Patient Controlled Drug Administration Device" issued Nov. 13, 2012 to Valle et al., the contents of each being incorporated herein by reference.

Downstream from the large volume bolus delivery system, continuous flow path 106 and the bolus dose flow path converge into a single flow path to patient P. An optional clamp and an optional filter may be positioned in the bolus flow path downstream from conduit 104. The clamp can compress the bolus flow path such that fluid flow from pump 102 is occluded. Such occlusion is advantageous for the transportation and preparation of fluid delivery device 100 as described herein.

The release-rate of the bolus dose to patient P is controlled by the decompression of the elastomeric bolus reservoir, by the pressure gradient at the actuator, and the diameter of the catheter 126. Advantageously, patient P does not have to provide pressure to force fluid out of the large volume bolus delivery system into the narrower bolus flow path. Rather, patient P can turn the stopcock or release the push button to administer the bolus dose. If patient P activates the bolus actuator or valve prior to the time the bolus reservoir has filled to its capacity, patient P receives less than the full amount of the bolus dose. In effect, this prevents the patient from self-administering more than the maximum desired amount of fluid per the time specified as a large volume bolus dose.

A flow detector assembly 122 with its flow detector may be located downstream of the location where continuous flow path 106 and the bolus dose flow path converge into a single flow path. In this location, the flow detector 122 provides a signal that the flow rate of the fluid in the single flow path is less than a predetermined flow rate; such a signal indicates a flow state that is less than a continuous and substantially constant flow rate of fluid.

Referring now to FIG. 2, flow selector 200 may be described in greater detail. Flow selector 200 sets the continuous and substantially constant flow rate of fluid from pump 102 to patient P via tubing 104. The flow rate may be adjusted to a rate within a range of from about 0.5 to about 14 cubic centimeters of fluid per hour. Desirably, the flow rate may be from about 0.5 to about 7 or from about 1 to about 12 cubic centimeters per hour. Flow selector 200 may be manually adjustable or may be automatically adjusted by a controller assembly or the like.

In the exemplary embodiment shown in FIG. 2, flow selector 200 includes a housing 202. A bottom half 202b of housing 202 is illustrated in FIG. 2; a top half complementary in shape to bottom half 202b completes housing 202. In other embodiments, however, housing 202 may have another configuration or may be omitted.

Flow selector 200 also includes an enclosure 204 for holding an inlet tube 206 and an outlet tube 208 (FIGS. 4, 7-10) in position relative to a flow rate selection mechanism 210 having a shaft 212. In some embodiments, inlet tube 206 may be the portion of conduit 104 providing ingress of the fluid to enclosure 204, and outlet tube 208 may be the portion of conduit 104 receiving egress of the fluid from enclosure 204. That is, separate inlet and outlet tubes 206, 208 may not be provided but, rather, may denote the portion of conduit 104 upstream and downstream, respectively, of enclosure 204. However, in other embodiments, inlet tube 206 and outlet tube 208 may be separate tubes connected to or in fluid communication with conduit 104 by any appropriate means such that continuous flow path 106 extends from conduit 104, through inlet tube 206, enclosure 204, and outlet tube 208 to conduit 104 downstream of flow selector 200 to deliver the fluid to patient P.

As illustrated in FIG. 2, in embodiments of flow selector 200 including housing 202, enclosure 204 is positioned within housing 202. In other embodiments, enclosure 204 may support and position inlet and outlet tubes 206, 208 and flow rate selection mechanism 210 with respect to each other such that housing 202 is not required or needed. Further, although illustrated as having a generally octagonal shape, enclosure 204 may have any appropriate or desired shape.

FIG. 3 provides an end view and FIG. 4 provides a top view of enclosure 204 according to an exemplary embodiment of the present subject matter. As illustrated in FIG. 3, enclosure 204 defines an inlet opening 206a for receiving inlet tube 206. Enclosure 204 further defines an outlet opening 208a for receiving outlet tube 208 and a shaft opening 212a for receiving shaft 212 of flow rate selection mechanism 210. Inlet opening 206a, outlet opening 208a, and shaft opening 212a may be defined at other locations or positions of enclosure 204, as further described below.

As shown in FIGS. 3 and 4, flow rate selection mechanism 210 may be disposed or positioned between inlet tube 206 and outlet tube 208. More specifically, a distal end 214 of flow rate selection mechanism 210, comprising a seat 218 for the receipt of shaft 212, may be positioned within enclosure 204 between inlet tube 206 and outlet tube 208. Positioning or disposing flow rate selection mechanism 210 between inlet tube 206 and outlet tube 208 permits an ingress of fluid into flow rate selection mechanism 210 from inlet tube 206 and an egress of fluid from flow rate selection mechanism 210 to outlet tube 208. In some embodiments, a cross or extension tube 220 may extend from inlet tube 206 to outlet tube 208, with flow rate selection mechanism 210 in fluid communication with cross tube 218 to receive an ingress of fluid from inlet tube 206 and permit an egress of fluid to outlet tube 208. In other embodiments, flow rate selection mechanism 210 may receive fluid directly from inlet tube 206 and may discharge fluid directly to outlet tube 208, i.e., inlet tube 206 and outlet tube 208 may be bent, curved, or otherwise positioned to permit direct fluid flow between tubes 206, 208 and flow rate selection mechanism 210.

FIG. 5 provides a perspective view and FIG. 6 provides a side view of flow rate selection mechanism 210 according to an exemplary embodiment of the present subject matter. As illustrated in FIGS. 5 and 6, flow rate selection mechanism 210 has distal end 214 and an opposing proximal end 216. Seat 218 is disposed at distal end 214 of flow rate selection mechanism 210 and receives a distal end 222 of shaft 212. That is, as shown in the cross-sectional view of FIG. 7, seat 218 comprises a recess 219 having a volume V. As illustrated in FIG. 8, recess 219 receives distal end 222 of shaft 212.

Referring back to FIGS. 5 and 6, shaft 212 extends along an axial direction A from a proximal end 224 to distal end 222. A threaded portion 226 connects shaft 212 and seat 218 and permits shaft 212 to rotate such that shaft 212 moves along axial direction A within seat 218, as further described below. However, it will be readily understood that threaded portion 226 is provided only by way of example. In alternative embodiments, shaft 212 and seat 218 may be connected in other ways and that shaft 212 may move axially with respect to 218 in other ways as well.

Flow rate selection mechanism 210 also includes a control knob 228 having a protruding portion 230; control knob 228 is positioned at proximal end 224 of shaft 212. Protruding portion 230 may, e.g., help a user of flow selector 200 visualize and/or keep track of the rotation of shaft 212 or help a user grip control knob 228 to manually adjust the flow rate using flow selector 200. Alternatively, control knob 228 may have other configurations, and in some embodiments, control knob 224 may be omitted, e.g., when flow selector 200 is automatically adjustable using a controller assembly or the like.

As shown in FIGS. 5, 6, 7, and 8, flow rate selection mechanism 210 may be a needle or pin valve. In such embodiments, distal end 222 of shaft 212 is tapered in shape, and recess 219 of seat 218 is shaped complementarily to the shape of distal end 222 of shaft 212. That is, recess 219, which is the portion of seat 218 that receives distal end 222 of shaft 212, is a tapered recess or generally frustoconical in shape. Other shapes of shaft 212 and recess 219 also may be used.

As previously stated, threaded portion 226 permits shaft 212 to rotate, e.g., through electromechanical means or by the application of a rotational force to control knob 228 by a user of flow selector 200. Shaft 212 is received within recess 219 of seat 218 such that, when rotated, shaft 212 may be advanced or retracted along the axial direction A within recess 219. That is, when rotated in one direction, shaft 212 advances toward distal end 214 of flow rate selection mechanism 210. When rotated in the opposite direction, shaft 212 retracts away from distal end 214. Thus, by rotating shaft 212, a smaller or larger portion of shaft 212 may be received within recess 219 of seat 218 such that more or less of volume V of recess 219 is occupied by shaft 212.

As described, flow rate selection mechanism 210 receives an ingress of fluid from inlet tube 206 and permits an egress of fluid to outlet tube 208. The fluid received at the inlet of flow rate selection mechanism 210 is at a relatively constant pressure, i.e., flow rate selection mechanism 210 is operated at relatively constant inlet pressures. Typical pressure profiles of the fluid encountered by flow rate selection mechanism 210 during its operation generally are as described at, e.g., U.S. Pat. No. 8,968,242 for "Inflatable Elastomeric Pump for an Infusion Assembly," issued Mar. 3, 2015 to Tefer, et al., the contents of which is incorporated herein by reference. Tefer, et al. illustrates pressure profiles of the fluid environment downstream of an elastomeric pump, which would be typical of the operating pressure profiles experienced by flow rate selection mechanism 210.

Referring now to FIG. 8, the flow of fluid from inlet tube 206 is received within recess 219 of flow rate selection mechanism 210, and the fluid fills an available volume $V_A$ of recess 219. The available volume $V_A$ is the open volume of recess 219 or the volume of recess 219 unoccupied by shaft 212. By rotating shaft 212 to move distal end 222 of shaft 212 along the axial direction A and thereby reposition distal end 222 within recess 219, the available volume $V_A$ may be adjusted.

In this way, flow selector 200 controls the flow rate within dispensing device 100. Rotating shaft 212 to advance distal end 222 toward distal end 214 of flow rate selection mechanism 210 decreases the available volume $V_A$ within recess 219, which decreases the flow rate of fluid through flow rate selection mechanism 210. Thus, the flow rate of fluid through selection mechanism 210 after advancing shaft 212 within recess 219 is less than the flow rate of fluid through selection mechanism 210 prior to such rotation of shaft 212. Rotating shaft 212 to retract distal end 222 away from distal end 214 of flow rate selection mechanism 210 increases the available volume $V_A$ within recess 219, which increases the flow rate of fluid through flow rate selection mechanism 210. Therefore, the flow rate of fluid through selection mechanism 210 after retracting shaft 212 within recess 219 is greater than the flow rate of fluid through selection mechanism 210 prior to such rotation of shaft 212. Accordingly, by rotating shaft 212, e.g., automatically or manually, a flow rate for the fluid downstream of flow rate selection mechanism 210 can be selected.

Constructing flow selector 200 as described above facilitates precise control of the flow rate within dispensing device 100. More particularly, the flow rate is adjustable on a continuous scale such that any appropriate flow rate, e.g., for intravenous or intramuscular drug delivery or for other applications of dispensing device 100, may be selected from zero flow to maximum flow, i.e., from no flow to the maximum flow rate attainable in the device. That is, even slight rotations of shaft 212 change the available volume $V_A$ of recess 219, which may change the flow rate of fluid through flow rate selection mechanism 210. Thus, the flow rate can be adjusted precisely and over an entire, continuous range of flow rate values, rather than a range of discrete flow rates.

In some embodiments, shaft 212 of flow rate selection mechanism 210 includes indicia 232 along shaft 212 for indicating a selected flow rate to a user of the flow selector 200. As illustrated in FIG. 6, indicia 232 may comprise a series of numbers representing a range of flow rates that may be selected using flow selector 200. The numbers are arranged sequentially along shaft 212 such that when shaft 212 is rotated and moves axially within seat 218, the portion of shaft 212 visible to the user indicates the current or selected flow rate. As previously described, the current or selected flow rate is based on the position of shaft 212 relative to seat 218; more particularly, the position of distal end 222 of shaft 212 within recess 219 of seat 218, which determines the available volume $V_A$ within recess 219 and thereby sets the flow rate through flow rate selection mechanism 210. In other embodiments, indicia 232 may be any means for indicating the selected flow rate to a user and/or may be provided on any appropriate feature or component of flow selector 200.

Referring now to FIGS. 9 through 12, schematic views of flow selector 200 are provided, illustrating various positions of inlet tube 206, outlet tube 208, and flow rate selection mechanism 210 within enclosure 204. As shown in each illustrated embodiment, enclosure 204 includes a first side 241, a second side 242, a third side 243, and a fourth side 244. First side 241 is opposite second side 242, and third side 243 is opposite fourth side 244. However, the illustrated embodiments are only exemplary configurations of enclosure 204; other configurations of enclosure 204 may be used as well.

Referring particularly to FIG. 9, in one exemplary embodiment, first side 241 of enclosure 204 defines inlet opening 206a and shaft opening 212a. Second side 242 of enclosure 204 defines outlet opening 208a. Thus, in the illustrated embodiment, inlet tube 206 and outlet tube 208 are disposed on opposite sides of enclosure 204, and shaft 212 of selection mechanism 210, having control knob 228, is disposed on the same side of enclosure 204 as inlet tube 206.

In the exemplary embodiment illustrated in FIG. 10, first side 241 of enclosure 204 defines inlet opening 206b. Second side 242 of enclosure 204 defines shaft opening 212b and outlet opening 208b. Thus, as shown in FIG. 10, inlet tube 206 and outlet tube 208 are disposed on opposite sides of enclosure 204, and shaft 212 of selection mechanism 210, having control knob 228, is disposed on the same side of enclosure 204 as outlet tube 208.

Referring now to FIG. 11, in another exemplary embodiment, first side 241 of enclosure 204 defines shaft opening 212c. Second side 242 of enclosure 204 defines inlet opening 206c and outlet opening 208c. Thus, in the illustrated embodiment of FIG. 11, inlet tube 206 and outlet tube 208 are disposed on the same side of enclosure 204, and shaft 212 of selection mechanism 210, having control knob 228, is disposed on the opposite side of enclosure 204 from inlet tube 206 and outlet tube 208.

As shown in FIG. 12, in another exemplary embodiment, inlet tube 206 and outlet tube 208 may be disposed on opposite sides of enclosure 204, and shaft 212 of selection mechanism 210, having control knob 228, may be disposed on a third side of enclosure 204 between inlet tube 206 and outlet tube 208. Such a configuration of inlet tube 206, outlet tube 208, and shaft 212 generally may be described and/or understood as a "T" configuration. More particularly, first side 241 of enclosure 204 defines inlet opening 206d. Second side 242 of enclosure 204 defines outlet opening 208d. Third side 243 defines shaft opening 212d, but in alternative embodiments, fourth side 244 may define shaft opening 212d. Whether third side 243 or fourth side 244 defines shaft opening 212d, shaft 212 having control knob 228 is disposed on a side of enclosure 204 that is between the side on which inlet tube 206 is disposed and the side on which outlet tube 208 is disposed.

It should be readily understood that references to first side 241, second side 242, third side 243, and fourth side 244 of enclosure 204 in FIGS. 9 through 12 are for convenience only. As discussed, these embodiments illustrate the various positions of inlet tube 206, outlet tube 208, and shaft 212 of flow rate selection mechanism 210 with respect to each other and enclosure 204. In some embodiments, inlet tube 206 and shaft 212 may be disposed on a side of enclosure 204 opposite outlet tube 208. In other embodiments, outlet tube 208 and shaft 212 may be disposed on a side of enclosure 204 opposite inlet tube 206. In still other embodiments, inlet tube 206 and outlet tube 208 may be disposed on a side of enclosure 204 opposite shaft 212. In alternative embodiments, inlet tube 206 may be disposed on a side of enclosure 204 opposite outlet tube 208, and shaft 212 may be disposed on a side of enclosure 204 between the sides on which inlet and outlet tubes 206, 208 are disposed. Of course, one of ordinary skill in the art will recognize that other configurations of inlet tube 206, outlet tube 208, shaft 212, and enclosure 204 also may be used.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

We claim:

1. A flow selector for selectively controlling a flow rate of a medicinal fluid, the flow selector comprising:
   an inlet tube;
   an outlet tube;
   a cross tube extending from the inlet tube to the outlet tube;
   a flow rate selection mechanism comprises a needle valve including:
      a shaft having a distal end and a proximal end, and
      a seat that receives the distal end of the shaft, the seat comprising a recess,
      wherein the recess is in fluid communication with the cross tube to permit an ingress of the medicinal fluid from the inlet tube into the recess and an egress of the medicinal fluid from the recess to the outlet tube, and wherein the shaft is configured to rotate such that the shaft moves along an axial direction into and out of the recess to control the flow rate of the medicinal fluid to the outlet tube to the selected flow rate by adjusting an available volume of the recess; and
   an enclosure for holding the inlet tube, the outlet tube, the cross tube, and the flow rate selection mechanism in position relative to each other, the enclosure having:
      an inlet opening for receiving the inlet tube,
      an outlet opening for receiving the outlet tube, and
      a shaft opening for receiving the shaft of the flow rate selection mechanism,
   wherein the seat is positioned within the enclosure, and
   wherein the inlet tube, outlet tube, and cross tube have the same inner diameter,
   wherein the flow-rate selection mechanism and the inlet tube are disposed in parallel orientation to each other in series along the cross-tube, and
   wherein a central axis of the flow-rate selection mechanism is substantially perpendicular to the cross-tube.

2. The flow selector of claim 1, wherein the shaft includes indicia for indicating a selected flow rate to a user of the flow selector,
   wherein the indicia are arranged along the shaft such that the indicia move into and out of the enclosure as the shaft rotates and moves along the axial direction with respect to the seat and a portion of the shaft visible to the user indicates the selected flow rate, wherein the indicia comprise a series of numbers disposed axially in series on the shaft representing a range of flow rates selectable using the flow selector.

3. The flow selector of claim 1, wherein the enclosure comprises an outer surface defining a first side and a second side, the second side being opposite the first side, and wherein the first side defines the inlet opening and the shaft opening and the second side defines the outlet opening.

4. The flow selector of claim 1, wherein the enclosure comprises an outer surface defining a first side and a second side, the second side being opposite the first side, and wherein the first side defines the inlet opening and the second side defines the outlet opening and the shaft opening.

5. The flow selector of claim 1, wherein the enclosure comprises an outer surface defining a first side and a second side, the second side being opposite the first side, and wherein the first side defines the inlet opening and the outlet opening and the second side defines the shaft opening.

6. The flow selector of claim 1, wherein the enclosure comprises an outer surface defining a first side, a second side, and a third side, the second side being opposite the first side and the third side being between the first side and the second side, and wherein the first side defines the inlet opening, the second side defines the outlet opening.

7. The flow selector of claim 1, wherein the proximal end of the shaft comprises a control knob.

8. The flow selector of claim 1, further comprising:
a housing,
wherein the enclosure is positioned within the housing.

9. The flow selector of claim 1, wherein the cross tube extends in a direction transverse to a longitudinal axis of both the inlet and the outlet tubes,
wherein the inlet tube, outlet tube, and cross tube have the same inner diameter.

10. The flow selector of claim 1, wherein the cross tube extends in a direction transverse to a longitudinal axis of both the inlet and the outlet tubes.

11. The flow selector of claim 1, further comprising a protruding portion extending from the shaft substantially perpendicular to a central axis of the shaft such that the protruding portion indicates a rotational position of the shaft.

12. The flow selector of claim 1, wherein the enclosure comprises an outer surface defining a first side and a second side, the second side being opposite the first side, and wherein the first side defines the inlet opening and the second side defines the outlet opening and the shaft opening.

13. A flow selector for selectively controlling a flow rate of a medicinal fluid, the flow selector comprising:
an inlet tube;
an outlet tube;
a cross tube extending from the inlet tube to the outlet tube;
a housing;
a needle valve including:
a shaft having a distal end and a proximal end, and a shaft threaded portion contiguous with the distal end, and
a seat that receives the distal end of the shaft,
wherein the distal end of the shaft is tapered in shape and the seat has a recess with a shape complementary to the shape of the distal end of the shaft, the recess defining a recess threaded portion extending around an entire circumference of at least a portion of the recess and corresponding to the shaft threaded portion and contiguous with a tapered distal end of the seat; and an enclosure for holding the inlet tube, the outlet tube, the cross tube, and the needle valve in position relative to each other, the enclosure having:
an inlet opening for receiving the inlet tube,
an outlet opening for receiving the outlet tube,
a first shaft opening for receiving the shaft of the needle valve, and
an outer surface defining a first side and a second side, the second side being opposite the first side, the first side defining the first shaft opening and either the inlet opening or the outlet opening, the second side defining the other of the inlet opening and the outlet opening,
wherein the distal end of the shaft is positioned between the inlet tube and the outlet tube within the enclosure to permit an ingress of the medicinal fluid from the inlet tube and an egress of the medicinal fluid to the outlet tube such that the needle valve is configured to permit the ingress of the medicinal fluid from the inlet tube into the recess and the egress of the medicinal fluid from the recess to the outlet tube,
wherein the recess is in fluid communication with the cross tube to permit an ingress of the medicinal fluid from the inlet tube into the recess and an egress of the medicinal fluid from the recess to the outlet tube,
wherein the shaft is configured to move along an axial direction into and out of the recess to adjust the flow rate of the medicinal fluid through the needle valve, and
wherein the enclosure is positioned within the housing, the housing defining a second shaft opening for receiving the shaft of the needle valve such that the shaft extends through the enclosure and the housing with the distal end of the shaft disposed within the enclosure and the proximal end of the shaft disposed outside of the housing.

14. The flow selector of claim 13, wherein the shaft of the needle valve comprises indicia for indicating a selected flow rate to a user of the flow selector.

15. The flow selector of claim 14, wherein the indicia comprise a series of numbers disposed axially in series on the shaft representing a range of flow rates selectable using the flow selector.

16. The flow selector of claim 13, wherein the shaft of the needle valve comprises a control knob for manual control of the flow rate of the medicinal fluid by a user of the flow selector.

17. The flow selector of claim 13, wherein the first side defines the inlet opening and the second side defines the outlet opening.

18. The flow selector of claim 13, wherein the first side defines the outlet opening and the second side defines the inlet opening.

19. The flow selector of claim 13, wherein an outer diameter of the proximal end of the shaft is greater than an outer diameter of the distal end of the shaft.

20. A flow selector for selectively controlling a flow rate of a medicinal fluid, the flow selector comprising:
an inlet tube;
an outlet tube;
a cross tube extending from the inlet tube to the outlet tube;
a flow rate selection mechanism including:
a shaft having a distal end, a proximal end, and including indicia for indicating a selected flow rate to a user, where the indicia comprise a series of numbers disposed axially in series on the shaft representing a range of flow rates selectable using the flow selector, and a seat that receives the distal end of the shaft, the seat comprising a recess, wherein the recess is in fluid communication with the cross tube to permit an ingress of the medicinal fluid from the inlet tube into the recess and an egress of the medicinal fluid from the recess to the outlet tube, and wherein the shaft is configured to rotate such that the shaft moves along an axial direction into and out of the recess to control the flow rate of the medicinal fluid to the outlet tube to the selected flow rate by adjusting an available volume of the recess; and an enclosure for holding the inlet tube, the outlet tube, the cross tube, and the flow rate selection mechanism in position relative to each other, the enclosure having:
an inlet opening for receiving the inlet tube,
an outlet opening for receiving the outlet tube, and
a shaft opening for receiving the shaft of the flow rate selection mechanism, wherein the seat is positioned within the enclosure, and wherein the inlet tube, outlet tube, and cross tube have the same inner diameter, wherein the flow-rate selection mechanism and the inlet tube are disposed in parallel orientation to each other in series along the cross-tube, and wherein a central axis of the flow-rate selection mechanism is substantially perpendicular to the cross-tube, wherein the indicia are arranged along the shaft such that the indicia move into and out of the enclosure as the shaft rotates and moves along the axial direction with respect to the seat and a portion of the shaft visible to the user indicates the selected flow rate.

21. The flow selector of claim 20, wherein the proximal end of the shaft comprises a control knob.

22. The flow selector of claim 20, wherein the enclosure comprises an outer surface defining a first side and a second side, the second side being opposite the first side, and wherein the first side defines the inlet opening and the shaft opening and the second side defines the outlet opening.

23. The flow selector of claim 20, wherein the enclosure comprises an outer surface defining a first side and a second side, the second side being opposite the first side, and wherein the first side defines the inlet opening and the outlet opening and the second side defines the shaft opening.

* * * * *